US00PP37117P2

(12) United States Plant Patent
Hansen

(10) Patent No.: US PP37,117 P2
(45) Date of Patent: Dec. 2, 2025

(54) ***ALLIUM* PLANT NAMED 'All the Buzz'**

(50) Latin Name: ***Allium* hybrid (L.)**
Varietal Denomination: All the Buzz

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,789

(22) Filed: Sep. 9, 2025

(51) Int. Cl.
*A01H 5/02* (2018.01)
*A01H 6/04* (2018.01)

(52) U.S. Cl.
USPC ..... Plt./242
CPC ..... *A01H 6/04* (2018.05)

(58) Field of Classification Search
USPC ..... Plt./242
CPC ..... A01H 5/02
See application file for complete search history.

*Primary Examiner* — Kent L Bell

(57) ABSTRACT

A new and distinct cultivar of *Allium* plant named 'All the Buzz' has a medium upright habit, with slightly glaucous, stiff, strap-like, upright, flattened, green foliage with slight longitudinal twisting. The tightly-clustered, light purple flowers forming a medium, globose, upright umbel. The new plant is useful for ornamental containers, landscaping and cut flowers.

2 Drawing Sheets

Botanical classification: *Allium* hybrid (L.).
Variety denomination: 'All the Buzz'.

STATEMENT REGARDING PRIOR DISCLOSURES UNDER 37 CFR 1.77(B)(6)

The first offer for sale of the claimed plant was Walters Gardens, Inc. to Hopewell Nursery, Inc. on Sep. 10, 2024. Walters Gardens, Inc. obtained the new plant and all information about the new plant directly from the inventor. No other plants of *Allium* 'All the Buzz' have been sold or offered for sale in this country or anywhere in the world nor has any disclosure of the new plant been made more than one year prior to the filing date of this application and such sale or disclosure within one year was either derived directly or indirectly from the inventor.

BACKGROUND AND ORIGIN OF THE PLANT

The present invention relates to the new and distinct ornamental onion, *Allium* 'All the Buzz' was developed by the inventor at a wholesale perennial nursery in Zeeland, Michigan, USA as the result of a self-pollination of 'Millenium' (not patented) in a greenhouse at a wholesale perennial nursery in Zeeland, Michigan on Jul. 1, 2018. Seeds from this pollination were collected in autumn of 2018 and were sown later that same year. The individual plant was originally selected from all seedlings from this pollination in the summer of 2018 and was given the breeder code 18-6-2 during the remaining trial period.

*Allium* 'All the Buzz' has been successfully asexually propagated by division method since 2020 at a wholesale perennial nursery in Zeeland, Michigan, and was found to be stable and produce identical plants that maintain the unique characteristics of the original plant through multiple generations.

SUMMARY OF THE PLANT

*Allium* 'All the Buzz' differs from its parents as well as all other ornamental onion known to the applicant. The most similar known *Allium* cultivars known to the inventor are: 'Lavender Bubbles' U.S. Plant Pat. No. 28,701, *Allium tanguticum* 'Summer Beauty' (not patented), and 'Serendipity' U.S. Plant Pat. No. 32,023.

'Lavender Bubbles' has a larger habit with dark dusky-purple flowers in larger inflorescences slightly later in the season. 'Summer Beauty' has a smaller habit with smaller umbel heads of pinkish-lavender flowers earlier in the summer. 'Serendipity' has a taller habit, dark rosy-purple flowers on smaller umbel heads about two weeks earlier than the new plant.

'Millenium' has a taller habit, bright rosy-purple flowers about two weeks earlier than the new plant with more green less-glaucous leaves.

*Allium* 'All the Buzz' differs from these above cultivars and all unregistered cultivars known to the inventor in the following combined traits:

1. Slightly glaucous, upright, stiff, strap-like, flattened, green foliage with slight longitudinal twisting;
2. Medium habit, drought tolerant, rabbit and deer resistant clumps;
3. Tightly-clustered light purple flowers in numerous globose umbels;
4. Strong stems hold flower head globes upright through flowering and seed production.

BRIEF DESCRIPTION OF THE DRAWINGS

The photographs of the new plant demonstrate the overall appearance of the plant, including the unique traits growing in a trial garden at a nursery in Zeeland, Michigan. The colors are as accurate as reasonably possible with color reproductions. Ambient light spectrum, source and direction may cause the appearance of minor variation in color.

DETAILED BOTANICAL DESCRIPTION

Figure 1:
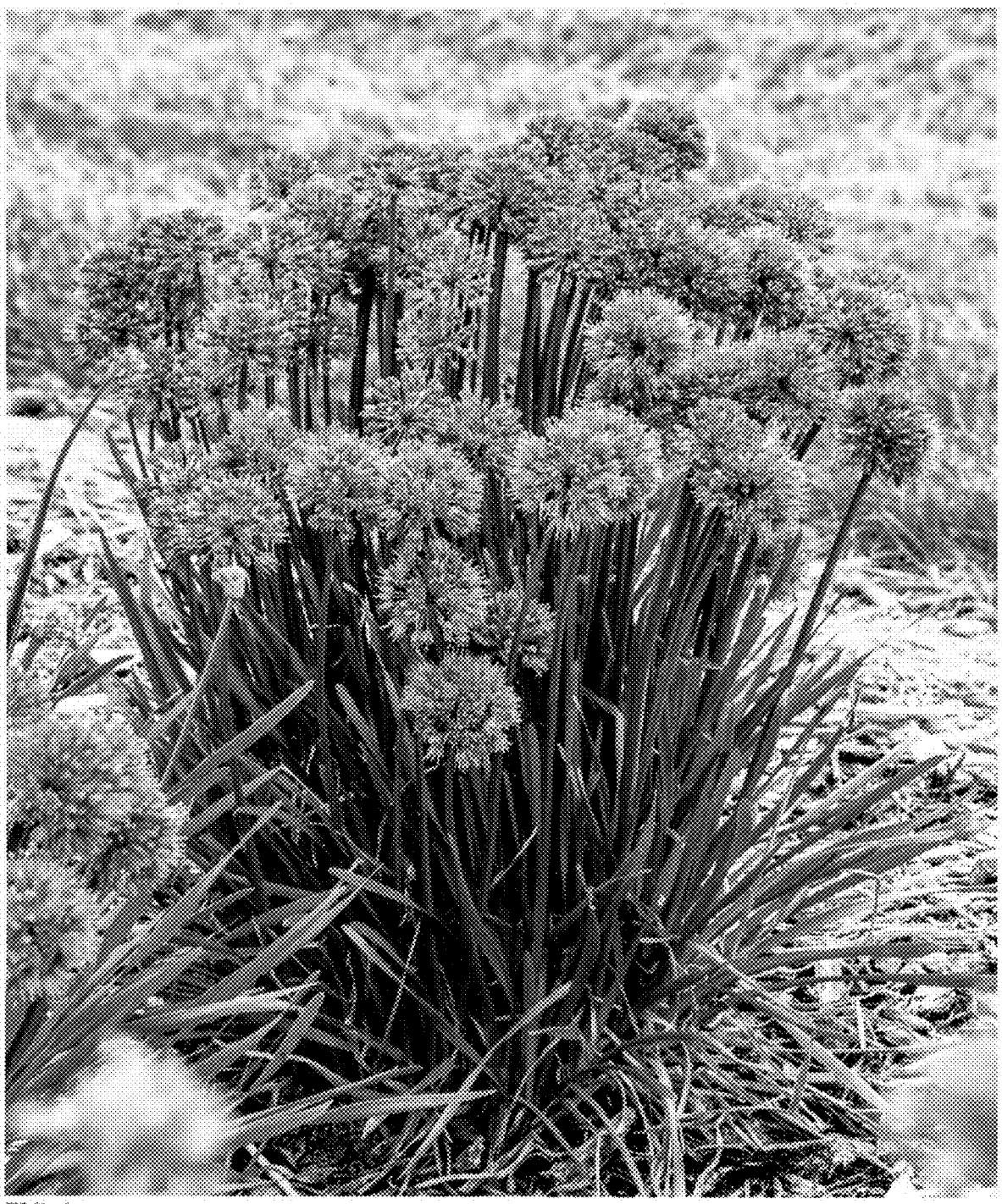
FIG. 1 shows the new plant habit of a three-year-old plant in early flowering in the foreground.
Figure 2:
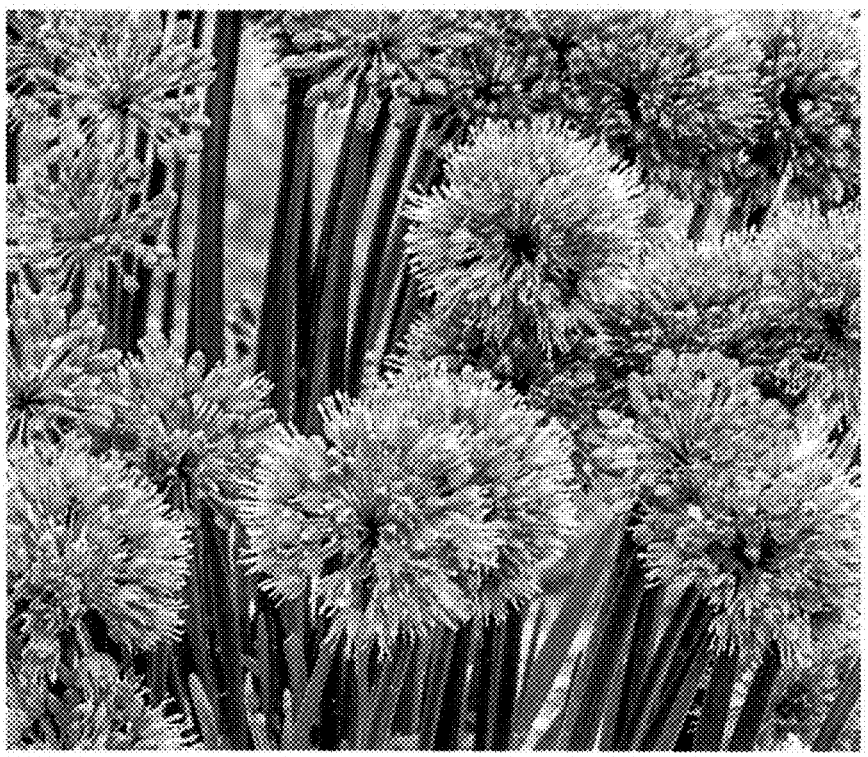
FIG. 2 shows a close-up of the umbels with flowers and buds.
Figure 3:
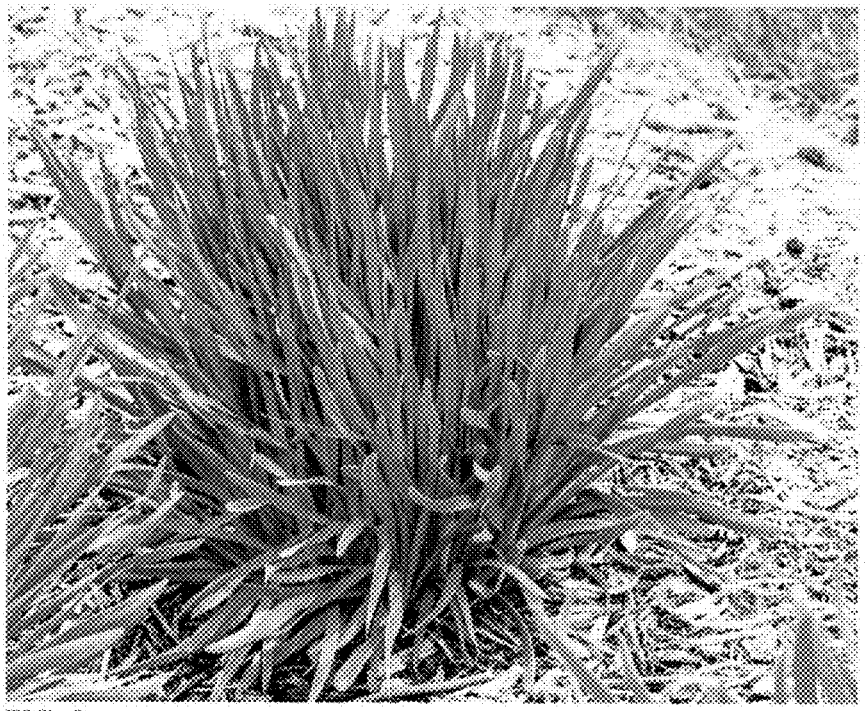
FIG. 3 shows a close-up of the foliage prior to flowering.

The following descriptions and color references are based on the 2015 edition of The Royal Horticultural Society Colour Chart except where common dictionary terms are used. The new plant, *Allium* 'All the Buzz', has not been observed under all possible environments. The phenotype may vary slightly with different environmental conditions, such as temperature, light, fertility, moisture, and maturity levels, but without any change in the genotype. The following observations and size descriptions are of a three-year-old plant in a trial garden of a wholesale perennial nursery in Zeeland, Michigan under full sun with supplemental water and fertilizer as needed.

Botanical classification: *Allium* hybrid;

Parentage: The parent was 'Millenium';

Propagation method: By division;

Growth rate: Vigorous, flowering in 3.8-liter containers in about 12 weeks;

Rooting habit: Fibrous from base of bulbs, lightly branching; color nearest RHS 158C;

Plant habit description: Dense clump of bulbs with sessile rosulate foliage about 66 cm across and about 33 cm tall; to about 90 inflorescences per plant; flowering to about 50 cm tall and about 39 cm across;

Bulbs: Elongated conical shape; about 5 cm long and 1.5 cm diameter at base; average about 75 per plant; color nearest RHS 155D;

Leaves: Sessile; linear; glaucous and becoming slightly lustrous later in the season; glabrous; semi-succulent; simple; margin entire; acute apex, truncate base, clasping on outer leaves; slightly twisted longitudinally around 180°; mostly flat; about 34 cm long, about 13 mm across near middle and to about 2.5 mm thick near middle; arranged in two-ranked tuffs from bulb; about 13 leaves per bulb; fragrance onion-scented;

Leaf color: Expanding adaxial and abaxial nearest RHS 144B with base nearest RHS N144D; mature adaxial and abaxial nearest RHS 137A distally with basal one-eighth transitioning to nearest RHS 145D;

Leaf venation: Parallel; color same as leaf abaxial and adaxial;

Inflorescence: In dense, terminal, globose umbel; about 80 to 100 flowers per inflorescence; about 5 cm across and about 4 cm tall; lasting about five weeks; beginning in mid-July to late August in Michigan;

Flower fragrance: Onion-like;

Blooming habit: One terminal umbel inflorescence per stem; with upright globe in bud, remaining upright as initial flowers open;

Buds one day prior to opening: Globose slightly flattened on three sides; rounded to truncate base, rounded apex; about 6 mm long and about 4 mm diameter at widest point near middle;

Bud color: Nearest RHS N75A;

Flowers: Campanulate; incomplete; perfect; with two sets of three tepals, outer set smaller than inner; superior ovary; actinomorphic; upward, outwardly, and drooping attitude depending on position in umbel; individually effective about four to six days; to about 9 mm long from base to exerted stamens and 7 mm across, corolla to about 6 mm tall and 7 mm across;

Tepals (outer set): Ovate to deltoid; convex; glabrous; lustrous; acute apex; truncate base; about 5 mm long and about 3 mm across;

Tepal (inner set): Ovate to deltoid; flat; glabrous; lustrous; acute apex, broadly acute base; about 6 mm long and to about 3.5 mm across;

Tepal color (inner and outer sets identical): Adaxial and abaxial nearly translucent to nearest, RHS 76C along margins and nearest RHS 76B in longitudinal center;

Pedicel: Cylindrical; stiff; upward, and outwardly, and drooping depending on orientation in umbel; glabrous; glaucous; about 14 mm long and about 0.8 mm diameter;

Pedicel color: Between RHS 138B and RHS 146B;

Peduncle: Glabrous, glaucous; flattened trapezoid to nearly ovoidal with two wings in cross-section and carinate with about 9 longitudinal ridges; to about 71 cm long, base about 8 mm wide and about 7 mm thick, middle portion about 6 mm wide and 5 mm thick;

Peduncle color: Basal 2 cm nearest RHS 145D, middle and distal portions nearest RHS 138A with carina nearest RHS 146C;

Gynoecium: Pistil single; to about 7 mm long;

*Style*.—Single; cylindrical; glabrous; upon early anthesis about 2.5 mm long and 0.5 mm diameter, lengthening to about 5 mm long and 0.5 mm across when mature, color between RHS 77D and RHS 75D.

*Stigma*.—Acute; about 0.2 mm across; color nearest RHS NN155C.

*Ovary*.—Distinctly tri-locule; each locule rounded at apex and truncate base; nearly cylindrical; about 2.5 mm long and 2.5 mm across; color between RHS N80C and RHS N80B at apex and between RHS 76D and RHS NN155D at base.

Androecium: Typically, six; exserted to about 9 mm long;

*Anther*.—Oblong; exserted about 1.5 mm long and about 0.5 mm wide; basifixed; longitudinal; color nearest RHS 199D.

*Filament*.—Glabrous; cylindrical distally, flattened in proximal 3 mm; to about 7 mm long and 0.7 mm across at base and about 0.3 mm diameter below anther; color nearest RHS 76D and lightening to between RHS 76D and RHS NN155D at base.

*Pollen*.—Abundant; color between RHS N187C and RHS N200C.

Fruit and seed: Not yet observed;

Disease and pest resistance: Ornamental onions typically resist deer and rabbit feeding. Resistance beyond that of other ornamental onions has not been observed.

*Allium* 'All the Buzz' plant grows best with good drainage and is able to tolerate some drought once established. Winter hardiness at least from USDA zone 4 through 8.

I claim:

1. A new and distinct cultivar of *Allium* plant named 'All the Buzz' as herein described and illustrated.

* * * * *